United States Patent
Ando et al.

(10) Patent No.: US 7,650,803 B2
(45) Date of Patent: Jan. 26, 2010

(54) BIOSIGNAL INTENSITY DISTRIBUTION MEASURING APPARATUS AND BIOSIGNAL INTENSITY DISTRIBUTION MEASURING METHOD

(75) Inventors: Mitsuhiro Ando, Toyohashi (JP); Shunsuke Kogure, Toyota (JP); Eiji Fujioka, Kariya (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 259 days.

(21) Appl. No.: 11/874,578

(22) Filed: Oct. 18, 2007

(65) Prior Publication Data

US 2008/0103702 A1    May 1, 2008

(30) Foreign Application Priority Data

Oct. 30, 2006   (JP)   ............... 2006-294548

(51) Int. Cl.
*G01L 1/00*   (2006.01)
(52) U.S. Cl. .................................. 73/862.391
(58) Field of Classification Search ............ 73/862.391
See application file for complete search history.

(56) References Cited

U.S. PATENT DOCUMENTS

| | | | | |
|---|---|---|---|---|
| 5,448,996 | A * | 9/1995 | Bellin et al. .............. | 600/574 |
| 5,724,990 | A * | 3/1998 | Ogino ....................... | 600/587 |
| 6,271,760 | B1 * | 8/2001 | Watanabe et al. .......... | 340/667 |
| 6,450,957 | B1 * | 9/2002 | Yoshimi et al. ............. | 600/309 |
| 6,505,522 | B1 * | 1/2003 | Wilssens ................... | 73/862.51 |
| 6,547,743 | B2 | 4/2003 | Brydon | |
| 6,852,086 | B2 * | 2/2005 | Atlas et al. ................ | 600/595 |
| 7,015,818 | B2 * | 3/2006 | Takashima ................ | 340/576 |
| 7,183,930 | B2 * | 2/2007 | Basir et al. ............... | 340/573.1 |
| 7,219,923 | B2 * | 5/2007 | Fujita et al. .............. | 280/735 |
| 7,409,868 | B2 * | 8/2008 | Ando et al. ............... | 73/778 |
| 7,482,938 | B2 * | 1/2009 | Suzuki ..................... | 340/576 |
| 2003/0233034 | A1 * | 12/2003 | Varri et al. ................ | 600/301 |
| 2006/0207341 | A1 | 9/2006 | Ando et al. | |
| 2007/0112283 | A1 * | 5/2007 | Ando et al. ............... | 600/587 |
| 2009/0069674 | A1 * | 3/2009 | Masumura et al. ........ | 600/425 |
| 2009/0199658 | A1 * | 8/2009 | ANDO et al. ............. | 73/862.59 |

FOREIGN PATENT DOCUMENTS

| | | |
|---|---|---|
| JP | 2001-525706 | 12/2001 |
| JP | 2006-258693 | 9/2006 |

* cited by examiner

*Primary Examiner*—Lisa M Caputo
*Assistant Examiner*—Freddie Kirkland, III
(74) *Attorney, Agent, or Firm*—Oblon, Spivak, McClelland, Maier & Neustadt, L.L.P.

(57) ABSTRACT

A biosignal intensity distribution measuring apparatus, includes a supporting member for supporting a human body, a plurality of detecting portions arranged in two dimensions within a target detection area of the supporting member, the detecting portions detecting pressure fluctuations and outputting signals corresponding to the pressure fluctuations respectively, a filter extracting a biosignal having a predetermined frequency band based from the signal outputted from each of the detecting portions, an intensity calculating portion calculating an intensity value of the biosignal, and an intensity distribution producing portion producing intensity distribution in which the intensity value corresponds to a position of the detecting portion.

20 Claims, 7 Drawing Sheets

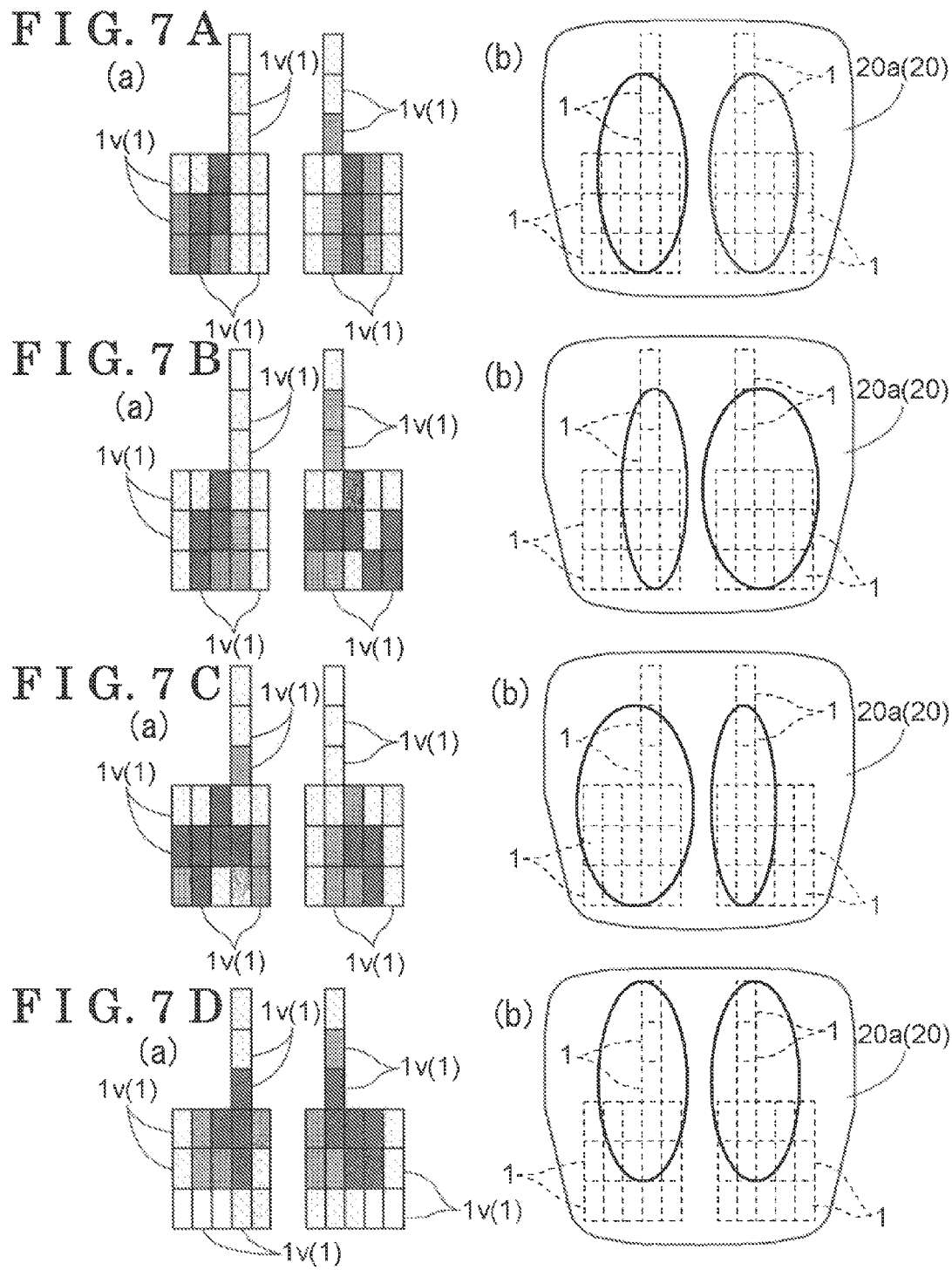

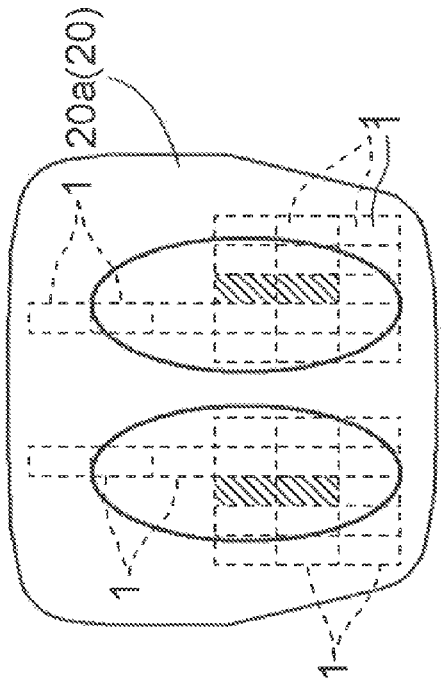
FIG. 8A
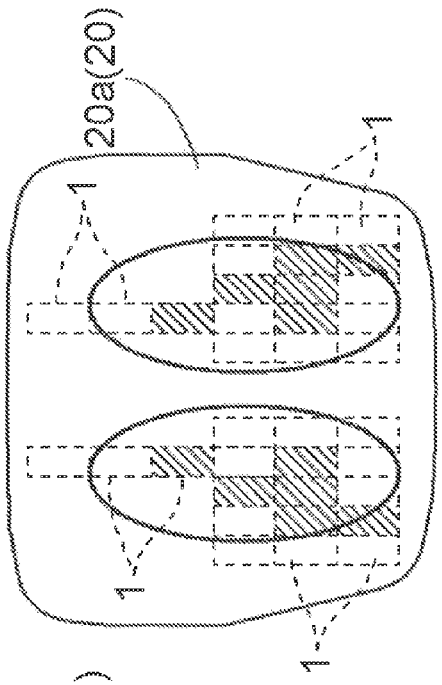
FIG. 8B
FIG. 8C
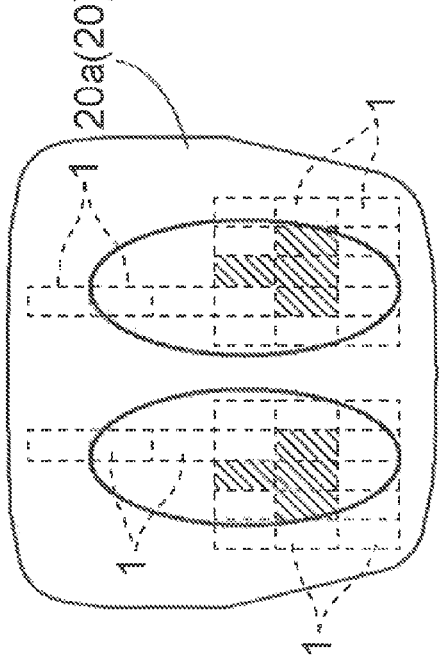
FIG. 8D

BIOSIGNAL INTENSITY DISTRIBUTION MEASURING APPARATUS AND BIOSIGNAL INTENSITY DISTRIBUTION MEASURING METHOD

CROSS REFERENCE TO RELATED APPLICATIONS

This application is based on and claims priority under 35 U.S.C. § 119 to Japanese Patent Application 2006-294548, filed on Oct. 30, 2006, the entire contents of which are incorporated herein by reference.

FIELD OF THE INVENTION

The present invention relates to a biosignal intensity distribution measuring apparatus and a biosignal intensity distribution measuring method of measuring a degree of biosignal intensity by using a plurality of detecting portions two-dimensionally provided at a supporting member that supports a human body.

BACKGROUND

It is known that a detecting device detects microvibration (biosignal) such as heartbeat and/or respiration of a human body that is supported by a supporting member such as a bed, a mattress or a seat. A detecting device having a plurality of sensor elements (detecting portions) at a supporting member for detecting microvibration is disclosed in JP2006258693A (paragraphs 26-30, and FIG. 8). The plurality of sensor elements are sequentially checked one by one in order to measure the microvibration within an area where the plurality of the sensor elements are provided. According to the detecting device disclosed in JP2006258693A, a large number of sensor elements are provided within a target area for detecting the microvibration. Therefore, measurement of the microbivration with higher resolution is achieved.

The detecting device disclosed in JP2006258693A measures the microbivration within the target area, therefore, the biosignal is detected without being largely influenced by a posture of the human body on the supporting member. However, it is not necessary to measure an entire target area for detecting the biosignal. In other words, some of the plurality of the sensor elements provided within the target area may not be necessary. Providing sensor elements that may not necessary for detecting the biosignal at the supporting member may increase manufacturing costs. However, the sensor elements that are necessarily arranged at the supporting member vary depending on to which supporting member the sensor elements are provided. Therefore, positioning of the sensor elements may not easily be determined.

A need thus exists for a biosignal intensity distribution measuring apparatus which is not susceptible to the drawback mentioned above.

SUMMARY OF THE INVENTION

According to an aspect of the present invention, a biosignal intensity distribution measuring apparatus, includes a supporting member for supporting a human body, a plurality of detecting portions arranged in two dimensions within a target detection area of the supporting member, the detecting portions detecting pressure fluctuations and outputting signals corresponding to the pressure fluctuations respectively, a filter extracting a biosignal having a predetermined frequency band based from the signal outputted from each of the detecting portions, an intensity calculating portion calculating an intensity value of the biosignal, and an intensity distribution producing portion producing intensity distribution in which the intensity value corresponds to a position of the detecting portion.

According to another aspect of the present invention, a biosignal intensity distribution measuring method, includes an arrangement process of two-dimensionally and dispersedly arranging a plurality of detecting portions within a target detection area of a supporting member that supports a human body, the detecting portions detecting pressure fluctuations and outputting signals corresponding to the pressure fluctuations respectively, a biosignal extracting process of extracting the biosignal from the signal outputted from the detecting portion, by filtering the signal having a predetermined frequency band through a filter, an intensity calculating process of calculating an intensity value of the biosignal detected by the detecting portion, an intensity distribution producing process of producing intensity distribution in which the intensity value corresponds to a position of the detecting portion, and an arrangement pattern producing process of producing an arrangement pattern of the detecting portion at the supporting member based upon the intensity distribution.

BRIEF DESCRIPTION OF THE DRAWINGS

The foregoing and additional features and characteristics of the present invention will become more apparent from the following detailed description considered with reference to the accompanying drawings, wherein:

FIG. 7A is an explanatory view illustrating connection between intensity distribution and a seated posture when the human body is seated in a normal posture;

FIG. 7B is an explanatory view illustrating connection between the intensity distribution and the seated posture when the human body is seated with applying more load to a right side of a seat cushion;

FIG. 7C is an explanatory view illustrating connection between the intensity distribution and the seated posture when the human body is seated with applying more load to a left side of the seat cushion;

FIG. 7D is an explanatory view illustrating connection between the intensity distribution and the seated posture when the human body is seated with applying more load to a front portion of the seat cushion;

FIG. 8 is an explanatory view illustrating an example of an arrangement pattern of the detecting portions.

DETAILED DESCRIPTION

Figure 1:
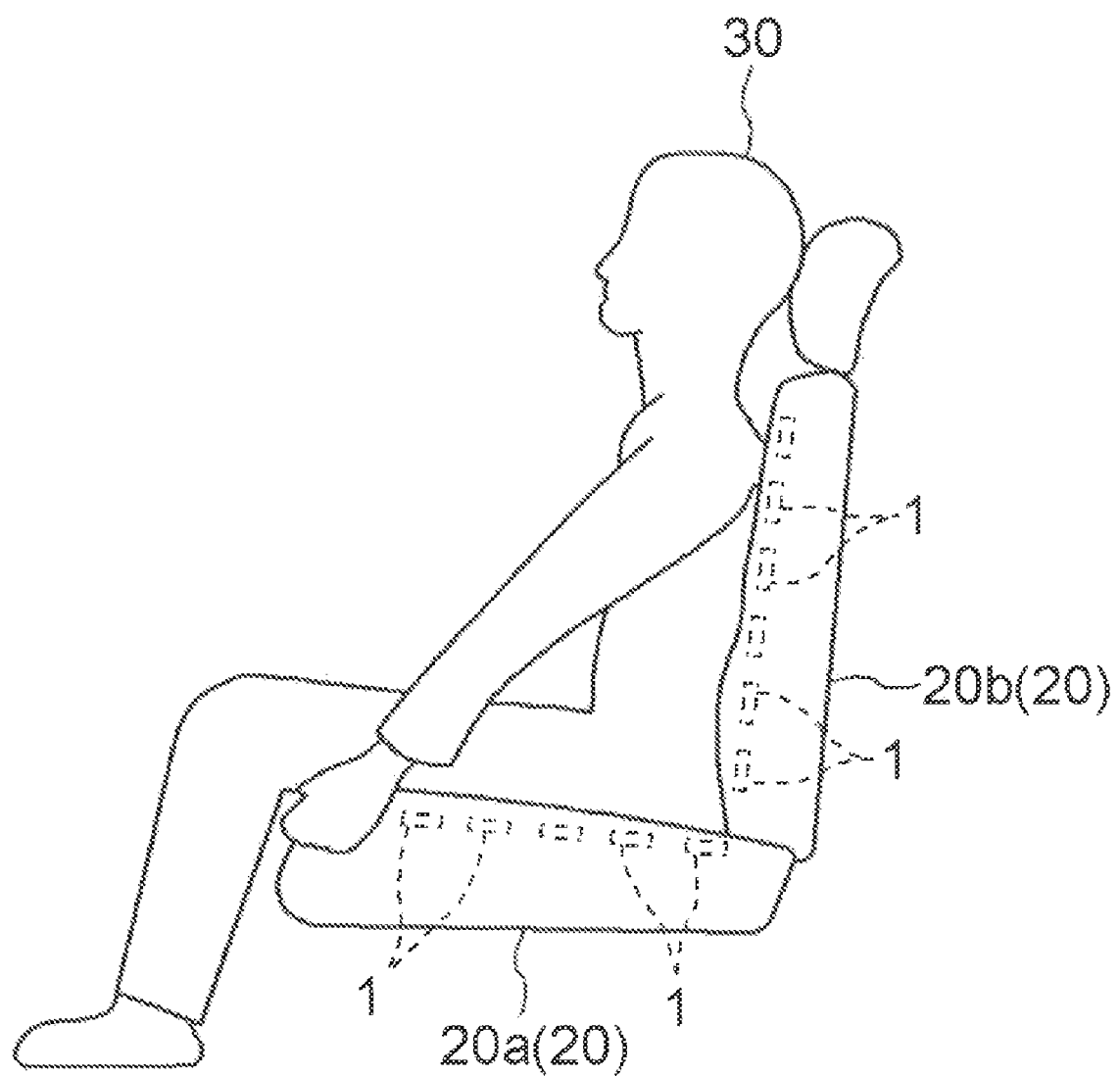
FIG. 1 is an explanatory view illustrating an example of a supporting member and detecting portions provided at the supporting member which are adopted for detecting a biosignal of a human body seated on the supporting member.

An embodiment of the present invention will be explained in accordance with the attached drawings. As shown in FIG. 1, sensors 1 (detecting portion) are provided at a seat cushion 20a and a seat back 20b of a seat 20 (supporting member) for detecting biosignals generated by a human body 30 seated on the seat 20. The sensors 1 are provided both at the seat cushion 20a and the seat back 20b in FIG. 1, however, the sensors 1 may be provided at either the seat cushion 20a or the seat back 20b. Moreover, the supporting member to which the sensors 1 are provided is not limited on the seat 20, but the sensors 1 are provided for a bed and the like.

Considering figure and posture of the human body 30, the sensors 1 are preferably provided two-dimensionally at a wider area in order to accurately detect the biosignal. However, all of the sensors 1 provided are not needed to detect the biosignals. Hence, in this embodiment, the biosignal intensity distribution measuring specifies necessary sensors 1 for detecting the biosignal.

Figure 2:
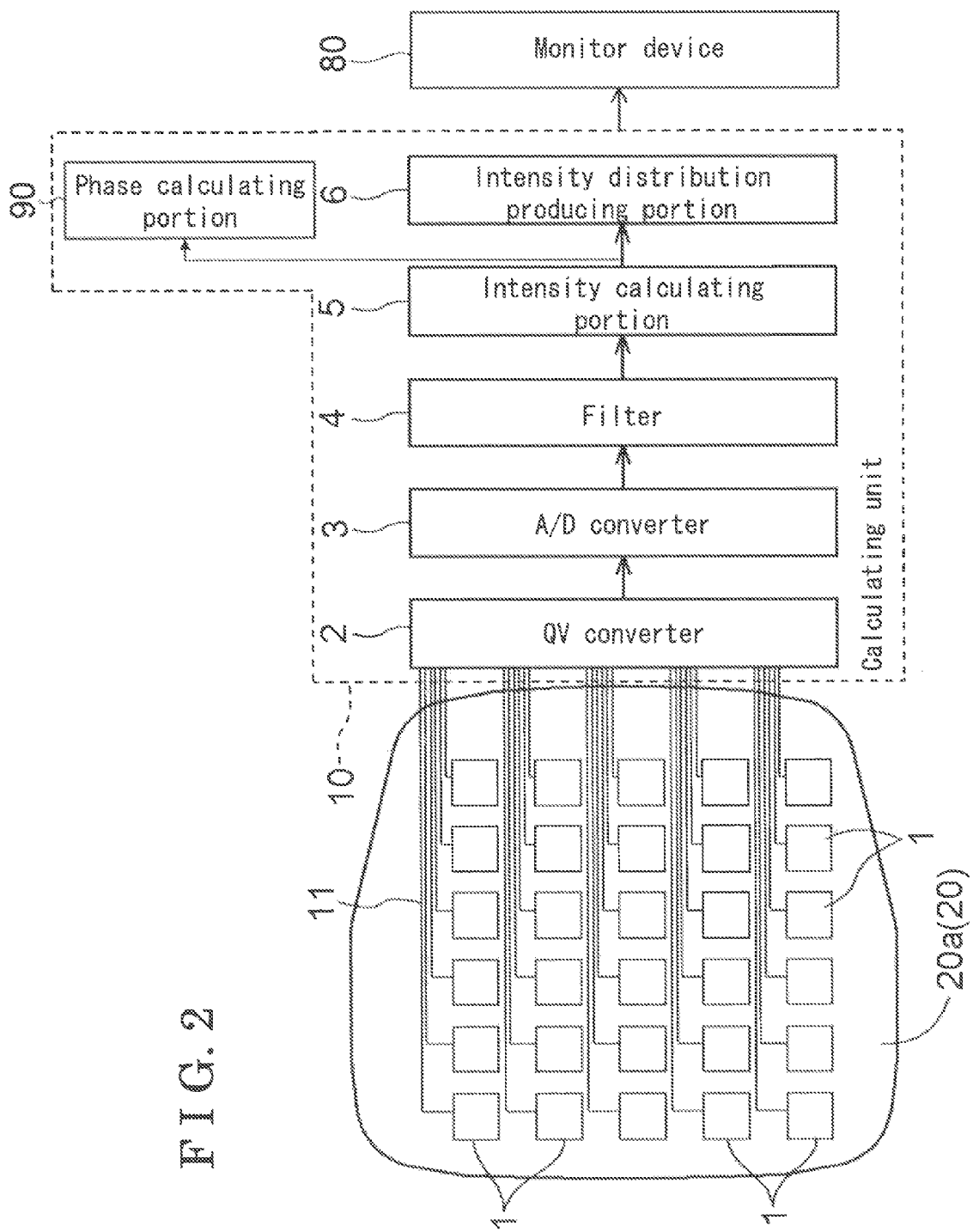
FIG. 2 is a block diagram schematically illustrating a configuration example of a biosignal intensity distribution measuring apparatus related to the present invention.

FIG. 2 is a block diagram schematically illustrating a configuration example of the biosignal intensity distribution measuring apparatus related to the embodiment. As shown in FIG. 2, in this embodiment, the sensors 1 are two-dimensionally provided at an inner side of an upper surface of the seat cushion 20a (arrangement process). For example, piezoelectric sensors are adopted as the sensors 1. The piezoelectric sensors generate electric charges when the piezoelectric sensors are strained (deformed) due to external force, such as load, oscillation, acceleration and the like, applied to the piezoelectric sensors. Then, the electric charges generated by the piezoelectric sensors are recognized as detecting signals of the load, the vibration, the acceleration and the like. Additionally, the sensors 1 are not limited on the piezoelectric sensors, but other sensors such as strain sensors may be adopted as the sensors 1.

As shown in FIG. 2, the sensors 1 provided at the seat cushion 20a are connected to a calculating unit 10 by means of wires 11. The calculating unit 10 includes a quantity-of-electricity to voltage value converter 2 (QV converter 2), an analog-to-digital converter 3 (A/D converter 3), a filter 4, an intensity calculating portion 5, an intensity distribution producing portion 6 and a phase calculating portion 90. The electric charges generated at the sensors 1 are converted into voltage signals W1 (outputted signals) at the QV converter 2. In this embodiment, the converted voltage signals W1 are further converted into digital signals at the A/D converter 3 because a further signal processing is executed by, for example, a microcomputer.

Figure 3:
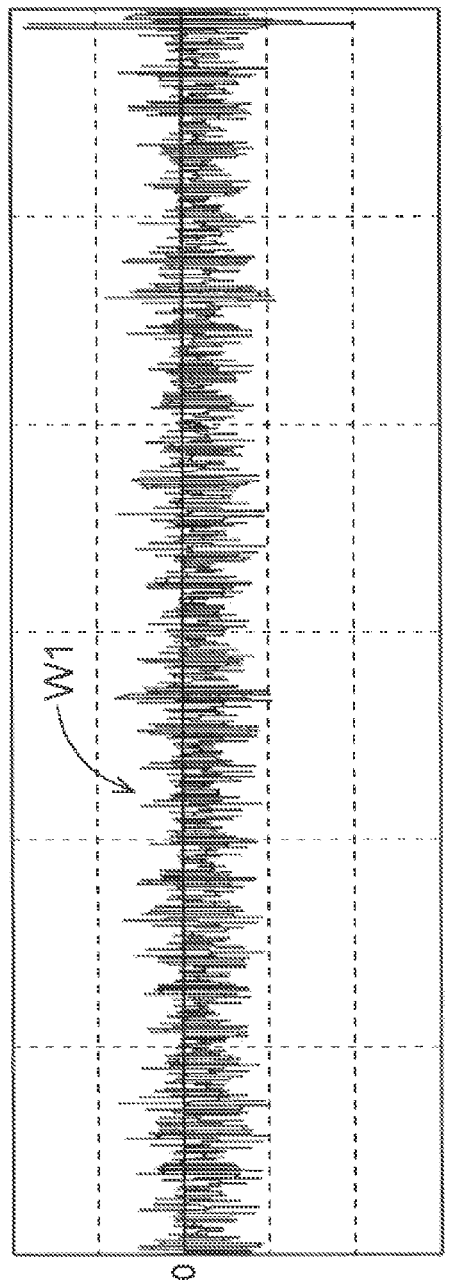
FIG. 3 is a waveform chart illustrating an example of a sensor output waveform after the QV conversion is completed.
Figure 4:
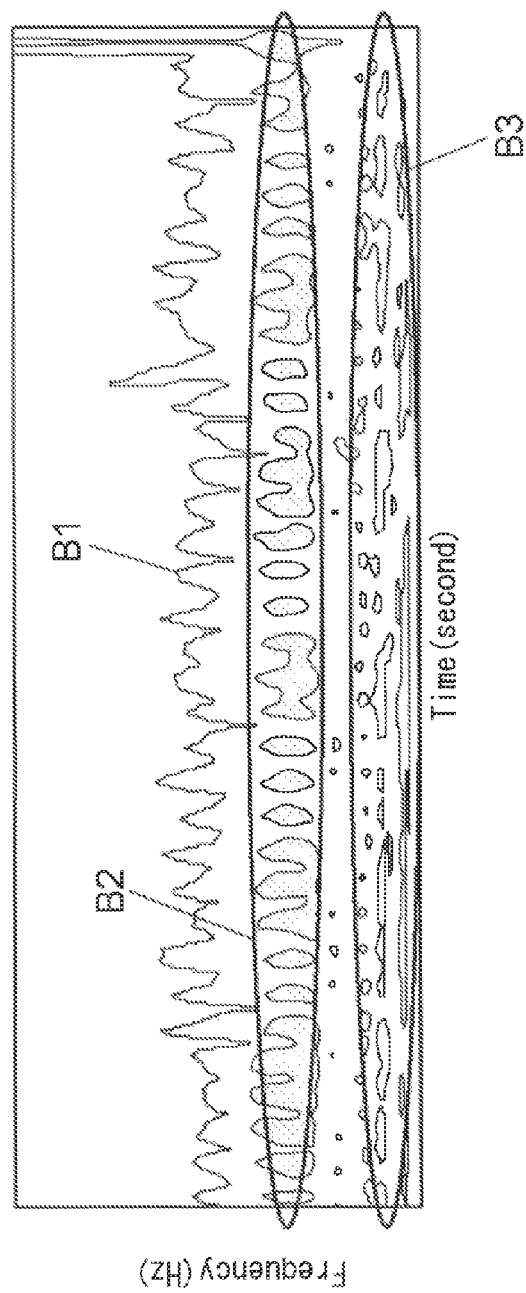
FIG. 4 is a waveform chart illustrating an example of result gained by applying the wavelet analysis to the sensor output waveform.

FIG. 3 is a waveform chart illustrating one of the voltage signals W1 that are generated by converting the electric charges at the QV converter 2. Various vibrations, such as vibration generated by noises, pulse (heartbeat) of the human body 30 and respiration, are superimposed on the voltage signal W1. FIG. 4 is a waveform chart schematically illustrating an example of results obtained when the voltage signal W1 is processed with the wavelet analysis. A band B1, whose band range is approximately more than, and equal to, 10 Hz, indicates a signal based on the vibrations generated by non-biosignal noises. A band B2, whose band range is approximately 4 to 7 Hz, indicates a signal based on the pulse (the biosignal). A band B3, whose band range is approximately 0.1 to 1 Hz, indicates a signal based on the respiration (biosignal).

Figure 5:
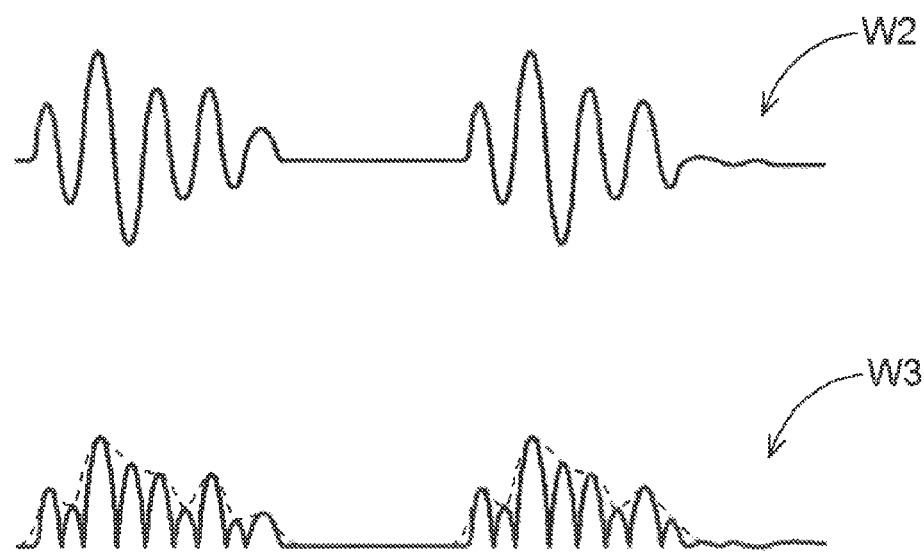
FIG. 5 is a waveform chart illustrating an example of method for evaluating intensity value of the biosignal.

As described above, each frequency band of the vibration generated by each vibration source differs from each other. Therefore, any desired signal is obtained by using an appropriate filter corresponding to the frequency band for filtering the oscillation. In this embodiment, the signal related to the pulse is extracted from various vibrations as the biosignal. Hence, the filter 4 is configured as, for example, a band-pass filter that passes the band of 4 to 7 Hz to the intensity calculating portion 5. As shown in FIG. 5A, the voltage signal W1 (see FIG. 3), in which various vibration components are superimposed, is filtered at the filter 4 and then transmitted to the intensity calculating portion 5 as a biosignal W2 (biosignal extracting process).

Additionally, calculation of an appropriate frequency band is not limited on applying the wavelet analysis, but the appropriated frequency band may be calculated by applying the Fourier analysis to the voltage signals W1. When the Fourier analysis is applied to the voltage signal W1, the voltage signal W1 is converted into series of sinusoidal wave function. Therefore, as is the case with the wavelet analysis, signal bands of vibrations, such as pulse, respiration and the noises contained in the voltage signal W1 are appropriately distinguished.

An intensity value of the biosignal W2 passed through the filter 4 is calculated at the intensity calculating portion 5. The intensity calculating portion 5 calculates the intensity value of the biosignal W2 by rectifying the biosignal W2 and then by calculating an envelope of the rectified biosignal W2 (intensity calculating process).

The intensity value of each sensor 1 is calculated in the above-mentioned manner. The intensity values of the sensors 1 are calculated by sequentially checking each of the sensors lone by one in chronological order, or the intensity values of the sensors 1 are concurrently calculated. When the intensity values of the sensors 1 are calculated by sequentially checking each of the sensors 1 one by one in chronological order, a selecting portion that determines order of checking each of the sensors 1 is provided before or after the QV converter 2. On the other hand, when the intensity values of the sensors 1 are concurrently calculated, the QV converter 1, the A/D converter 3, the filter 4 and the intensity calculating portion 5 vary in numbers depending on the number of the sensors 1 provided at the seat 20.

In this embodiment, the biosignal extracting process and the intensity calculating process are implemented by firstly applying the A/D conversion to the signal to which the QV conversion is applied, and secondly applying the digital signal processing using, for example, the microcomputer to the A/D converted signal. However, the biosignal extracting process and the intensity calculating process are not limited on the above-mentioned manner, but the process up to the intensity calculating process may be completed by an analog signal processing and then applying the A/D conversion to the gained intensity values. Additionally, each portion illustrated in FIG. 2 only shows functional division and does not necessarily show physical independence of each of the portions. As long as each function is divided within hardware or software, such as programs, run on hardware, the calculating unit 10 is achieved.

When the intensity value of each of the sensors 1 is calculated in the above-mentioned manner, as two-dimensional arrangement of the sensors 1 is well-know, an intensity distribution of the biosignal received at the two-dimensionally arranged sensors 1 is produced at the intensity distribution producing portion 6 (intensity distribution producing process). Examples of the intensity distribution produced at the intensity distribution producing portion 6 is described below in accordance with the case where two-dimensional arrangement of the plurality of sensors 1 on the seat cushion 20a is illustrated, as shown in FIG. 6.

Figure 6:
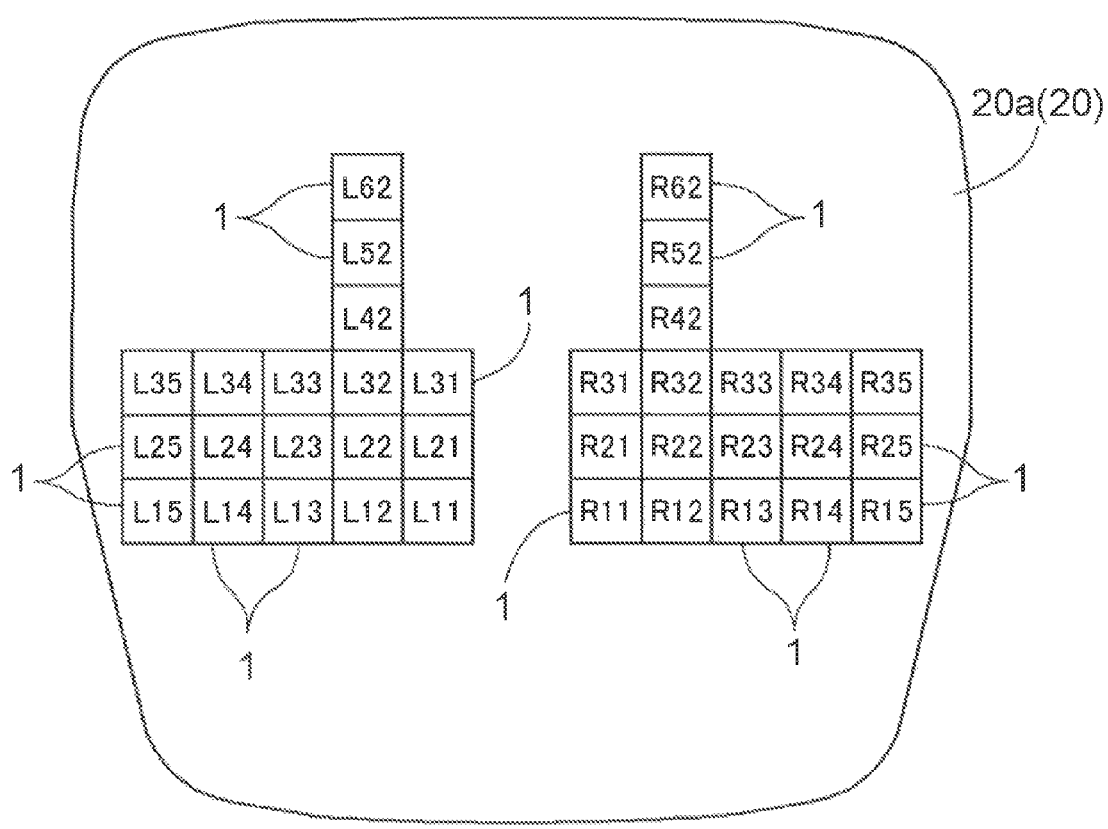
FIG. 6 is an explanatory view illustrating an example of a two-dimensional arrangement of the detecting portions at the supporting member.

The sensors 1 are provided on the seat cushion 20a so as to be separated into right and left as shown in FIG. 6. In FIG. 6, sensors 1 are provided at positions in which the glutei and the left and right femoral regions of the human body contact the seat cushion 20a. Codes, such as L11 and R11 in FIG. 6 indicate identification codes of each of the sensors 1. The upside of FIG. 6 indicates front of the seat cushion 20a, the downside of FIG. 6 indicates the rear of the seat cushion 20a, the sensors 1 having the identification codes starting with L indicate a group of sensors provided at the left of the seat cushion 20a, and the sensors 1 having the identification codes starting with R indicate a group of sensors provided at the right of the seat cushion 20a.

Distribution of the intensity of biosignal received at the sensors 1 provided in the above-mentioned manner is illustrated in FIG. 7. The intensity of the biosignal is schematically illustrated with four-level color tones in the left half of FIG. 7. The darker colored sensors 1 indicate that intensity of the biosignal is stronger. The right half of FIG. 7 schematically illustrates the intensity of loads applied by the femoral regions of the human body 30 to the seat cushion 20a. In FIG. 7A, distribution illustrated in (a) indicates a case where the human body 30 is seated in a normal posture with the both glutei and femoral regions applying load equally to the seat 20 as shown in (b). In FIG. 7B, distribution illustrated in (a) indicates a case where the human body 30 is seated in a posture with applying more load to right of the seat 20 as shown in (b). In FIG. 7C, distribution illustrated in (a) indicates a case where the human body 30 is seated in a posture with applying more load to left of the seat 20 as shown in (b). In FIG. 7D, distribution illustrated in (a) indicates a case where the human body 30 is seated in a position with the human body 30 applying more load to the front portion of the seat 20 as shown in (b). The distributions illustrated in FIGS. 7A, 7B, 7C and 7D, are displayed on, for example, a monitor device 80 included at the biosignal intensity distribution measuring apparatus. In this embodiment, the intensity distribution is displayed with four level color tones of a specified color (in this embodiment, black is used), however, the color tones may be graded in more levels. Additionally, the intensity distribution may be displayed in colors.

As shown in FIG. 7, the sensors 1 showing the strong intensity of the biosignal vary depending on the seated posture of the human body 30. However, intensity indications 1v corresponding to, for example, the sensors 1 having the identification codes L33, L23, L23, R33 and R23, show relatively high intensity in any cases. Hence, the biosignal is well detected when at least those sensors 1 are provided at the seat 20 despite the seated posture of the human body 30.

The sensors 1 necessary for accurate detection of the biosignal are selected by an operator who visually confirms the intensity distribution, for example, shown in FIG. 7, on the monitor device. However, the necessary sensors 1 may be selected by the operator after the intensity distribution is quantified as shown in FIG. 8. In other words, the intensity distribution producing portion 6 may quantify the intensity distribution so that the quantified intensity distribution is displayed on the monitor device 80.

FIG. 8A illustrates the integrated intensity of the biosignal when the human body 30 is seated at the four postures described in FIG. 7. In this embodiment, intensity values 1, 2, 3 and 4 are given so as to correspond to intensities in four levels in increasing order. As shown in FIG. 8A, quantified values 1u corresponds the identification codes L33, L23, L24, R33 and R23 all exceed 10. Therefore, the biosignal is accurately detected despite the postures of the human body 30 when at least those sensors 1 showing more than 10 quantified values are provided at the seat 20. The result is the same as in a case where the sensors necessary for the accurate biosignal detection is selected based on the intensity indications 1v. However, quantifying the intensity distribution reduces errors caused by the operator in selecting necessary sensors 1. As a result, further accurate selection of the necessary sensors 1 is achieved.

Additionally, the intensity values are integrated in the above-mentioned example, however, the intensities of the biosignal may be displayed by weighting. For example, numbers such as 8, 4, 2 and 1 may be given so as to correspond to the intensity in decreasing order. Additionally, the weighting is given so as to correspond to frequency of the posture the human body 30 takes when the human body 30 is seated. For example, frequency of the human body 30 being seated in the normal posture is described with the weighting 6, frequency of the human body 30 being seated with applying more load to either the right or the left femoral regions is described with the weighting 4, and frequency of the human body 30 being seated with applying more load to the front portion of the seat 20 is described with the weighting 2.

Figure 9:
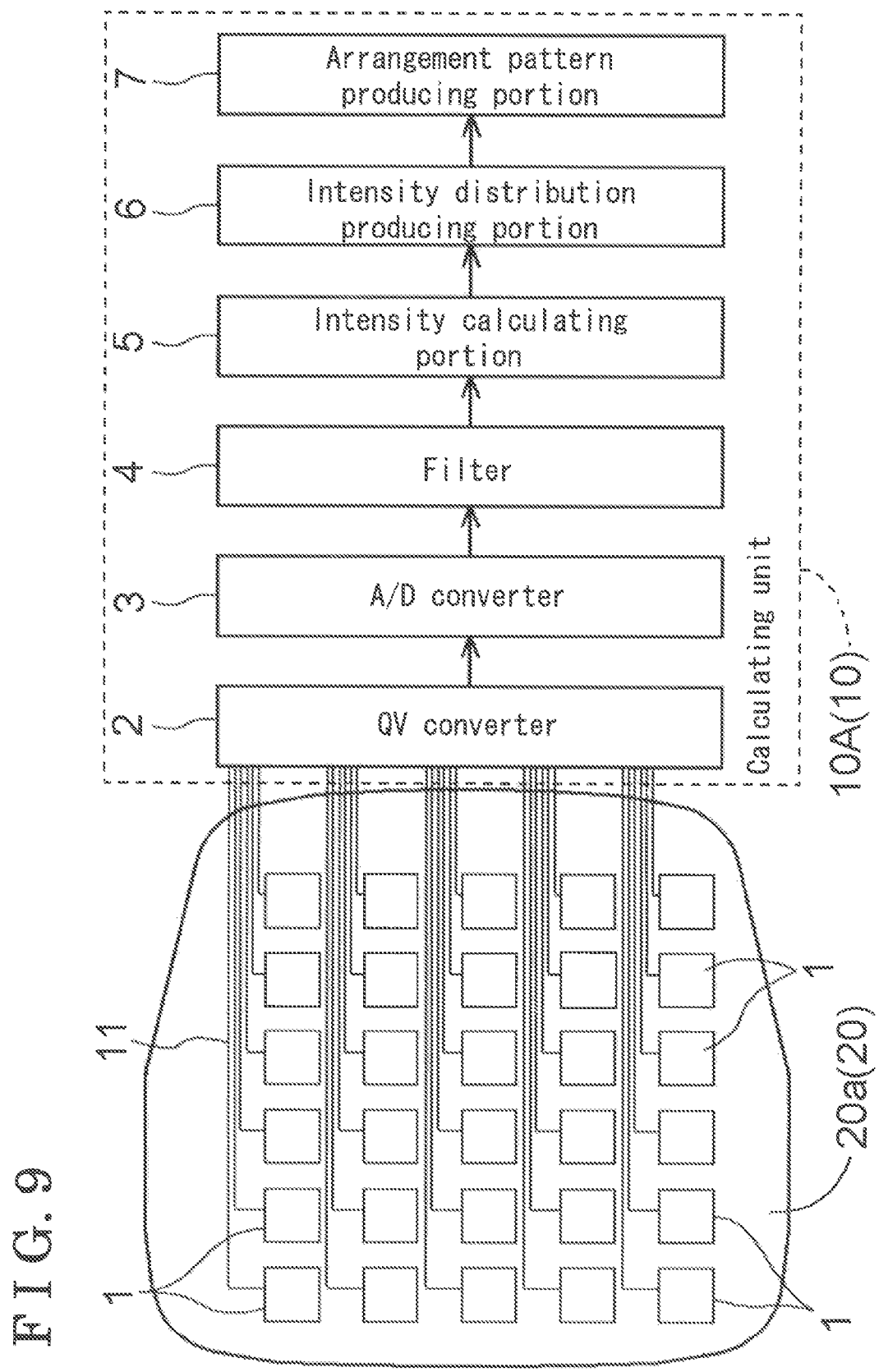
FIG. 9 is a block diagram schematically illustrating another configuration example of the biosignal intensity distribution measuring apparatus related to the present invention.

The appropriate position of the sensors 1 at the seat 20 is automatically determined by quantifying the intensity distribution. FIG. 9 illustrate an example of a configuration of an calculating unit 10A when an arrangement pattern producing portion 7 for determining arrangement of the sensors 1 is included to the calculating unit 10 illustrated in FIG. 2.

The arrangement pattern producing portion 7 determines the intensity of the biosignal received at each of the sensors 1 based on a threshold set to the quantified value 1u. For example, when the threshold is set to 10 for the quantified values shown in FIG. 8A, the sensors 1 having the identification codes L33, L23, L24, R33 and R23 are determined as the necessary sensors 1 for accurate detection of the biosignal. In this embodiment, three sensors 1 provided at the left half of the seat 20 and two sensors 1 provided at the right half of the seat 20 are determined as necessary sensors 1. In a case where load balance between the right half and the left half of the seat 20 is not considered, positions of those 5 sensors 1 are determined as the arrangement pattern.

In a case where the load balance between the right half and the left half of the seat 20 is considered, positions of the sensors 1 having the identification codes L33, L23, R33 and R23, which are symmetrically provided at the seat 20, are determined as the arrangement pattern. Alternatively, the quantified value 1u of the sensor 1 having the identification code R24 that corresponds to the sensor 1 having the identification codes L24 may be re-evaluated. In the example shown in FIG. 8, the quantified value 1u of the sensor 1 having the identification code R24 is 9, which is slightly below 10. Hence, positions of the sensors 1 having the identification codes L33, L23, L24, R33, R23 and R24 may be determined as the arrangement pattern.

Upper limit and lower limit may be set for the number of sensors 1 determined as the necessary sensors 1 for accurate detection of the biosignal. When the number of sensors 1 determined in the above-mentioned manners does not reach the upper limit, the threshold of the quantified value u1 may be decreased in order to increase the number of sensors 1 determined as the necessary sensors 1 for the accurate detection of the biosignal. When the number of sensors 1 exceeds the upper limit number of sensors 1, the threshold of the quantified value u1 may be raised in order to decrease the number of sensors 1 determined as the necessary sensors 1 for the accurate detection of the biosignal. For example, when the upper limit of the number of sensors 1 is set to 10, and the lower limit of the number of sensor 1 is set to 6, further, when the threshold of the quantified value 1 is set to 10, the number of sensors 1 is lower than the lower limit 6 in the arrangement pattern illustrated in FIG. 8B. When the threshold of the quantified value u1 is set to 8, an arrangement pattern illustrated in FIG. 8D is adopted, however, the arrangement pattern in FIG. 8D exceeds the upper limit 10 of the number of sensors 1. When the threshold of the quantified value u1 is set to 9, the number of the sensors 1 determined as the necessary sensors 1 is 8, which falls within a range between the upper limit and the lower limit of the number of the sensors 1.

As described above, the arrangement pattern producing portion 7 produces the arrangement pattern based on various setting conditions (arrangement pattern producing process).

Additionally, the intensity distribution producing portion 6 calculates a pseudo-intensity value between the neighboring sensors 1 based on the intensity value of each of the sensors 1 in order to complement intensity value of a space where the sensor 1 is not provided. The sensors 1 are arranged at the seat 20 so as to be spaced from each other, as shown in FIG. 2. As the supporting member, such as the seat 20 and the bed, has structural limitations, the sensors 1 are not always arranged at the position arranged for the embodiment when the intensity distribution is measured. When the arranged position of the sensors 1 in this embodiment is not adaptable to other supporting members that have a different structure from the seat 20 in this embodiment, re-measurement of the intensity distribution is generally implemented. However, the re-measurement of the intensity distribution takes time for arrangement planning and manufacturing. Hence, the intensity distribution producing portion 6 calculates the pseudo-intensity value between the neighboring sensors 1 based on the intensity value of each of the sensors 1 in order to avoid the re-measurement of the intensity distribution.

An average intensity value of the two neighboring sensors 1 or an average intensity value of the four neighboring sensors 1 is used as the pseudo-intensity value. The average intensity value of the four neighboring sensors 1 is an average intensity value of four sensors 1 located around a targeted point for calculating the pseudo-intensity value. By complementing the intensity value to space, where the sensors 1 are not provided, with the pseudo-intensity value, determination of the arrangement pattern of the sensors 1 are not limited on the positions arranged when the intensity values of the sensors 1 are measured, but the appropriate arrangement of the sensors 1 are determined for configurations of any supporting member.

Additionally, as well as the calculating unit 10, the calculating unit 10A may include a phase calculating portion (not shown in FIG. 9). Time when each of the sensors 1 receives the biosignal differs because the sensors 1 are two-dimensionally provided at the seat 20. In other words, time when each of the sensors 1 detects the biosignal differs, even in a case where the identical biosignal is a targeted signal to be detected. However, by calculating a relative phase at the phase calculating portion 90, the calculating unit 10 determines whether time difference between a biosignal detecting time at one of the sensors 1 provided at the seat 20 and a biosignal detecting time at another one of the sensors 1 is appropriate or not. When the calculating unit 10 determines that the time difference is not appropriate, there is a possibility that signals other than the target signal are detected at the sensors 1. Hence, providing the phase calculating portion 90 contributes to increase detection performance of the biosignal As described in the abovementioned embodiment, the biosignal intensity distribution measuring apparatus that determines appropriate arrangement of the detecting portions two-dimensionally and dispersedly provided at a target area for detecting the biosignal is achieved.

According to the embodiment, the intensity distribution, in which the intensity values correspond to the positions of the sensors 1 two-dimensionally and dispersedly provided within the target detection area, is produced. The sensors 1 necessary for accurate detection of the biosignal is determined based on the intensity distribution. Therefore, the biosignal intensity distribution measuring apparatus that determines the appropriate arrangement of the sensors 1 is achieved.

According to the embodiment, the filter 4 is a band-pass filter that filters a frequency calculated by means of the wavelet analysis or the Fourier analysis.

The frequency band for detecting any desired biosignal is accurately set by means of the wavelet analysis and the Fourier analysis. Hence, as the band-pass filter, which passes the necessary frequencies of the any desired frequency band, is configured, the accurate intensity distribution may be obtained.

According to the embodiment, the intensity distribution producing portion 6 calculate pseudo-intensity value between the neighboring sensors 1 based upon the intensity value detected by each of the sensors 1.

Accordingly, when the actual measurement of the intensity values are conducted, not only the intensity values the sensors 1 detect, but the pseudo-intensity values between the neighboring sensors 1 are also calculated. Hence, appropriate arrangement of any structures of the supporting members is determined without being limited on the positions the sensors 1 arranged at the seat 20 when the intensity values are measured.

According to the embodiment, the biosignal intensity distribution measuring apparatus includes a phase calculating portion 90 that calculates relative phase of the biosignal.

The time the biosignal propagated to the sensors 1 differs from each other because the sensors 1 are two-dimensionally arranged at the seat 20. In other words, even in a case where the identical biosignal is detected, the time for each of the sensors 1 to detect the biosignal differs from each other. However, according to the embodiment, the relative phase of the biosignal between the neighboring sensors 1 are obtained. The calculating unit 10 determines whether time difference between the biosignal detecting time of one of the sensors 1 provided at the seat 20 and the biosignal detecting time of another one of the sensors 1 is appropriate or not by using the relative phase. When the calculating unit 10 determines that the time difference between the detecting time the one of the sensors 1 detects the biosignal and the detecting time the another one of the sensors 1 detects the biosignal is not appropriate, the calculating unit 10 determines that the sensors 1 may detect other signals due to noises and the like. Hence, according to the embodiment, the accurate detection of the biosignal is achieved.

According to the embodiment, the appropriate arrangement of the sensors 1, which are two-dimensionally and dispersedly provided within the targeted detection area, is determined by using the biosignal intensity distribution measuring method described above. Additionally, the biosignal intensity distribution measuring method may include additional characteristics and effects generated by the additional characteristics of the biosignal intensity distribution measuring apparatus.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the sprit of the present invention. Accordingly, it is expressly intended that all such variations, changes and equivalents which fall within the spirit and scope of the present invention as defined in the claims, be embraced thereby.

The invention claimed is:

1. A biosignal intensity distribution measuring apparatus, comprising:
    a supporting member supporting for a human body;
    a plurality of detecting portions arranged in two dimensions within a target detection area of the supporting member, the detecting portions detecting pressure fluctuations and outputting signals corresponding to the pressure fluctuations respectively;
    a filter extracting a biosignal having a predetermined frequency band based from the signal outputted from each of the detecting portions;
    an intensity calculating portion calculating an intensity value of the biosignal; and
    an intensity distribution producing portion producing intensity distribution in which the intensity value corresponds to a position of the detecting portion.

2. The biosignal intensity distribution measuring apparatus according to claim 1, wherein the supporting member includes a seat cushion.

3. The biosignal intensity distribution measuring apparatus according to claim 1, wherein the detecting portion includes a piezoelectric sensor.

4. The biosignal intensity distribution measuring apparatus according to claim 1, wherein the biosignal is a pulse related signal.

5. The biosignal intensity distribution measuring apparatus according to claim 1, further comprising a monitor device displaying the intensity distribution.

6. The biosignal intensity distribution measuring apparatus according to claim 1, wherein the intensity distribution is displayed with color tone of a specified color.

7. The biosignal intensity distribution measuring apparatus according to claim 1, wherein the predetermined frequency band is obtained with either of Wavelet Analysis and Fourier Analysis and the filter is in the form of a band pass filter allowing various frequencies in the signal to pass.

8. The biosignal intensity distribution producing apparatus according to claim 1, wherein the intensity distribution producing portion calculates pseudo-intensity value between the neighboring detecting portions based on the intensity value detected by the detecting portion.

9. The biosignal intensity distribution producing apparatus according to claim 1, further comprising a phase calculating portion that calculates relative phase of the biosignal.

10. A biosignal intensity distribution measuring method, comprising;
    an arrangement process of two-dimensionally and dispersedly arranging a plurality of detecting portions within a target detection area of a supporting member that supports a human body, the detecting portions detecting pressure fluctuations and outputting signals corresponding to the pressure fluctuations respectively;
    a biosignal extracting process of extracting the biosignal from the signal outputted from the detecting portion, by filtering the signal having a predetermined frequency band through a filter;
    an intensity calculating process of calculating an intensity value of the biosignal detected by the detecting portion;
    an intensity distribution producing process of producing intensity distribution in which the intensity value corresponds to a position of the detecting portion; and
    an arrangement pattern producing process of producing an arrangement pattern of the detecting portion at the supporting member based upon the intensity distribution.

11. A biosignal intensity distribution measuring apparatus comprising:
    a supporting member for supporting thereon a human body;
    a plurality of detecting elements arranged in two dimensions within a target detection area of the supporting member, each of the detecting elements detecting a change of a pressure applied thereto and outputting such a pressure change as a signal in which vibrations of different frequencies are superposed;
    a filter extracting one of the different frequencies of the signal which falls in a predetermined frequency band and specifying one of the vibrations having the resulting frequency as a biosignal;
    an intensity calculating portion calculating an intensity value of the biosignal coming from each of the detecting elements; and
    an intensity distribution producing portion producing intensity distribution for relating the intensity value of the biosignal to a position of each of the detecting elements.

12. The biosignal intensity distribution measuring apparatus as set forth in claim 11, wherein the supporting member is a seat cushion.

13. The biosignal intensity distribution measuring apparatus as set forth in claim 11, wherein each of the detecting elements is a piezoelectric sensor.

14. The biosignal intensity distribution measuring apparatus as set forth in claim 11, wherein the biosignal is a pulse related signal.

15. The biosignal intensity distribution measuring apparatus as set forth in claim 11 further comprising a monitoring device which displays the intensity distribution.

16. The biosignal intensity distribution measuring apparatus as set forth in claim 15, the intensity value is displayed with a variety of densities of a single color.

17. The biosignal intensity distribution measuring apparatus as set forth in claim 11, wherein the predetermined frequency band is obtained with either of Wavelet Analysis and Fourier Analysis and the filter is in the form of a band pass filter allowing various frequencies in the signal to pass.

18. The biosignal intensity distribution measuring apparatus as set forth in claim 11, wherein the intensity distribution producing portion, on the basis of the intensity value of one of the detecting elements, calculates a psuedo-intensity value between one of the detecting elements and its adjacent detecting element.

19. The biosignal intensity distribution measuring apparatus as set forth in claim 11 further comprising a phase calculating portion calculating a relative phase between selected two of the biosignals.

20. A method of measuring biosignal intensity distribution comprising the steps of:
    arranging a plurality of detecting elements in two dimensions within a target detection area of a supporting member in order that when a person sits on the supporting member each of the detecting elements detects a change of a pressure applied thereto to output such a pressure change as a signal in which vibrations of different frequencies are superposed;

filtering one of the different frequencies of the signal which falls in a predetermined frequency band in order to specify one of the vibrations having the resulting frequency as a biosignal;

calculating an intensity value of the biosignal coming from each of the detecting elements;

producing intensive distribution relating the intensity value of the biosignal to a position of each of the detecting elements and producing an allocation pattern of detecting elements at the supporting potion on the basis of the intensive distribution.

* * * * *